United States Patent
Voris et al.

(10) Patent No.: US 7,056,522 B2
(45) Date of Patent: *Jun. 6, 2006

(54) SUSTAINED RELEASE PEST CONTROL PRODUCTS AND THEIR APPLICATIONS

(75) Inventors: Peter Van Voris, Richland, WA (US); Dominic A. Cataldo, Kennewick, WA (US); Edward S. Lipinsky, Worthington, OH (US)

(73) Assignee: Termiguard Technologies, Inc., Kennewick, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/993,611

(22) Filed: Nov. 27, 2001

(65) Prior Publication Data

US 2002/0086044 A1 Jul. 4, 2002

Related U.S. Application Data

(63) Continuation-in-part of application No. 09/347,704, filed on Jul. 3, 1999, now Pat. No. 6,322,803.

(51) Int. Cl.
*A01N 25/26* (2006.01)

(52) U.S. Cl. .................. 424/419; 424/405; 424/406; 424/407; 424/408; 424/417; 424/420; 514/124; 514/531

(58) Field of Classification Search ................ 424/405, 424/406, 407, 408, 417, 419, 420; 523/122; 514/124, 531
See application file for complete search history.

(56) References Cited

U.S. PATENT DOCUMENTS

| | | | | |
|---|---|---|---|---|
| 5,708,073 A | * | 1/1998 | Dodge et al. | ................ 524/590 |
| 5,801,194 A | * | 9/1998 | Voris et al. | ................ 514/531 |
| 6,322,803 B1 | * | 11/2001 | Van Voris et al. | .......... 424/406 |

FOREIGN PATENT DOCUMENTS

GB 1288583 * 9/1972

* cited by examiner

*Primary Examiner*—Neil S. Levy
(74) *Attorney, Agent, or Firm*—Mueller and Smith, LPA

(57) ABSTRACT

A method for applying a barrier to structures to prevent the infiltration of pest species (unwanted organisms) uses a (e.g., coating) composition formed from a polyurethane (e.g., film-forming) polymer system and a pellet comprising a pesticide incorporated into a sorbent and dispersed in the polyurethane polymer system. The composition protects the structure by application either to the structure or to a pathway that leads to the structure. Advantageous polymer systems include polyurethanes rich in urea linkages and predominating in aliphatic and alicyclic backbones.

21 Claims, 1 Drawing Sheet

SUSTAINED RELEASE PEST CONTROL PRODUCTS AND THEIR APPLICATIONS

CROSS-REFERENCE TO RELATED APPLICATIONS

This application is a continuation-in-part of application Ser. No. 09/347,704 filed on Jul. 3, 1999, now U.S. Pat. No. 6,322,803, this disclosure of which is expressly incorporated herein by reference.

STATEMENT REGARDING FEDERALLY SPONSORED RESEARCH

Not applicable.

BACKGROUND OF THE INVENTION

The present invention relates generally to a method for applying and delivering pesticides, insecticides, and repellents to structures, surfaces of structures, and materials important to commerce and industry, and more particularly to polyurethane polymer systems containing pesticide(s) and or pellets containing bioactive active chemicals having extremely long useful lives.

Wood and wood products utilized in a variety of construction applications are frequently structurally degraded by the action of termites, ants, other boring insects, and wood decaying microorganisms. Typically, these wood degrading and decaying organisms migrate to wood structures via the surrounding soil or water. This migration may occur whether the structures rest upon concrete foundations, such as in wooden building construction; are in direct contact with the soil, for example fence posts, utility poles, railroad cross-ties, wooden supports, and like structures; or are in the water, such as boats, piers, pier pilings, wooden docks, or other supports. Wood and wood-containing products include, inter alia, glued wood products such as, for example, plywood, particleboard, oriented strand board (OSB), medium density fiberboard (MDF), laminated veneer lumber (LVL), laminated beams, and a variety of other engineered wood products. Paper products (especially paperboard and kraft paper) also are subject to degradation by organisms that attack wood. Outdoor furniture also is subject to wood degrading and decaying organisms. In the marine context (including for example, pleasure and commercial craft for use on lakes and oceans), the structures additionally may be manufactured from fiberglass, various plastics, metals, ceramics, and other materials.

Present methods of preventing or retarding the advance of these wood degrading organisms include soil treatment with pesticides and repellent chemicals, treatment of the wood with chemicals, and fumigation wherein the entire structure may be sealed and a pesticide pest repellent released. Both soil and fumigation type treatments may release the pesticide to the surrounding atmosphere and/or the pesticide may move to ground water where it may harm human beings or other living organisms. Disadvantages of these methods of treating soil and/or fumigating include, inter alia, potential ecological and human health concerns, as well as the limited time until the fumigant or soil concentration is sufficiently reduced in concentration to permit ingress of wood degrading organisms.

Although many pesticides and repellents are known to be effective against the action of wood destroying organisms, their effectiveness often declines over time as they are dissipated into the surrounding environment (soil, water, or atmosphere) or are degraded, for example, chemically or biologically. To retain their effectiveness, these insecticides must be repeatedly applied at regular intervals ranging from every few days to every few months to every few years. Alternatively, if the pesticides and repellents are applied in sufficient quantity to be effective over an extended period of time, the ecological and human health related concerns associated with these chemicals and their unpleasant odors are exacerbated. Furthermore, with the banning of certain chemicals and the introduction of safer shorter half-life compounds, even large amounts of many of these pesticides and repellents may be required over a relatively short time periods, and they will need to be reapplied more often.

A further disadvantage of conventional application methods is that the concentration of pesticides and repellents resulting from a single application starts out well above the minimum concentration necessary for effectiveness, but decreases rapidly. Within a relatively short period of time the concentration drops below the minimal effective level necessary to maintain a barrier to the invasion of wood compromising organisms.

To overcome these problems, a number of techniques for the controlled release of chemicals, such as insecticides, have been proposed. These methods employ polymer matrices and microcapsules used to contain insecticide and allow the slow release of the pesticides and repellents over extended time periods. One such scheme is found in U.S. Pat. No. 4,400,374, which discloses the use of polymer matrices generally made of polyethylene, polypropylene, ethylene vinyl acetate, polyamide, polystyrene, polyvinyl acetate, or polyurethane to control the release of insecticides such as the insecticide commercially available under the trade name DURSBAN. The polymer matrices disclosed in U.S. Pat. No. 4,400,374, incorporate a porosigen and a porosity reducing agent, which upon contact with soil moisture or an aqueous environment dissolves the matrix. Similarly, U.S. Pat. No. 4,405,360 proposes a polymer release matrix, which can be composed of polyamide, polyurethane, polyethylene, polypropylene, polystyrenes, or other polymers. The control release mechanism works in combination with a porosigen to release a herbicide in a moist environment. A disadvantage of both of these methods is the necessity of sufficient moisture to dissolve the matrix. Periods of dryness, while extending the life of the matrix, results in a decrease in the insecticide concentration, thereby permitting insects to have access to the wooden structure. In addition, the longevity of the matrix is variable and dependent upon moisture content.

U.S. Pat. No. 4,435,383 proposes the use of a controlled release mechanism for insecticides including carbamates, organothiophosphates, organophosphates, perchlorinated organics, and synthetic pyrethroids. The release mechanism comprises a hydrophobic barrier that is a polymer prepared from styrene and/or methyl styrene in combination with a monomer selected from one or more unsaturated mono- or di-carboxylic acids. U.S. Pat. No. 5,860,266 proposes the preparation of construction sites with plastic sheets impregnated with an insecticide.

U.S. Pat. No. 4,282,209 proposes a process for the preparation of insecticide-polymer particles. The insecticide, methomyl, is used to control insects, which attack tobacco, cotton, or other agricultural crops. Methomyl is dissolved into polymers, such as polyamides, urethanes, or epoxies, to provide extended residual insecticidal activity. U.S. Pat. No. 4,235,872 proposes the use of slow-release insecticide microcapsules having a core of methomyl surrounded by a cover of all-aromatic, un-crosslinked polyurea to protect vegetables, field crops, and fruit crops.

U.S. Pat. No. 4,198,441 proposes the use of insecticides, such as chlorpyrofos (DURSBAN) in a controlled release matrix comprising an organopolysiloxane, a hydrolyzable silane, and a hydrolyzable organic titanium compound. U.S. Pat. No. 4,160,335 proposes a mode of dispersing insect control substances by applying stripes to sheets of cellophane. The insect control substance, which can include DURSBAN, is placed in a polymer as well.

Australian patent AU-B-82443/91 proposes to use two sheets of plastic drawn from supply rolls, wherein the upper face of the lower sheet and the lower face of the upper sheet are drawn past respective coating rollers which apply a coating of pesticide (e.g., permethrin) in a volatile solvent to the faces of the sheets. The coated faces of the sheets are brought together by passing them between compressive rollers. The coated and pressed sheets are laid under building foundations or placed around trees or plants to prevent termite attack. Disadvantages of this product and method include (1) delamination permits rapid escape of the coating, and (2) the coating is not integral to the sheets, thereby permitting faster diffusion through the sheets and limiting the effective life.

Coated granules have a pesticide absorbed onto a matrix, such as clay, and then coated with cross-linked resins which helps slow the release rate. Clay loses or releases pesticide over a short period of at most a few weeks.

In U.S. Pat. No. 5,801,194, a controlled release device is disclosed, which incorporates insecticide into polymer materials to form a device, which then may be placed in and around wooden structures to form an effective exclusion zone lasting several years or more. The reported extended effectiveness is accomplished by using of low volatility insecticide within a high-density polymer, the combination having a low release rate of the insecticide. While the '194 patent does describe a device that provides long lasting protection against insect penetration, the application of this device to either new or existing structures requires the manual placement of the device in and around those structures. The application of the device in this manner may be time consuming, labor intensive, and expensive. In one embodiment of the '194 patent, the controlled release device is placed into a polyurethane foam to allow the spray application of the device to wooden structures. While this approach does lessen the labor, and thus the cost associated with placing the device in contact with the structures that need to be protected, it does have other drawbacks. For example, at the time the device is applied to the structure, the insecticide is not adequately dispersed throughout the volume of the polyurethane foam. This results in a lack of protection from invasive insects during the time period required for the insecticide to permeate the polymer and infiltrate the foam. To overcome this drawback, the '194 patent also proposes combining the low volatility insecticide within a high-density polymer with a more volatile insecticide within a low-density polymer which has a higher release rate. The drawbacks of this combined system include the potential harm to human and other life forms, which may occur as a result of their coming into contact with the more volatile insecticide.

Japanese 62236937 proposes the use of a polyol/isocyanate/pesticide/microparticle solution that is painted or sprayed upon the surface of the foundation and the ground around the foundation. Inclusion of the microparticles creates gaps between the particles. The gaps are filled with the pesticide containing urethane polymer. Therefore, the urethane polymer containing the microparticles acts as a sponge and enables the release of the pesticide without trapping it. By the varying of the amount of microparticles, the applicator can change the rate of the pesticide release.

Thus, there exists a need for improved pesticide control agents for protecting wooden structures, which improved control agents provide immediate, as well as long lasting, protection from, inter alia, termites, ants, wood boring insects, and other wood destroying microorganisms. It is to such improved pesticide control agents that the present invention is addressed.

BRIEF SUMMARY OF THE INVENTION

A method for applying a barrier to structures to prevent the infiltration of pest species (unwanted organisms) uses a (e.g., coating) composition formed from a polyurethane (e.g., film-forming) polymer system and a pellet comprising a pesticide incorporated into a sorbent and dispersed in the polyurethane polymer system. The composition protects the structure by application either to the structure or to a pathway that leads to the structure. Advantageous polymer systems include polyurethanes rich in urea linkages and predominating in aliphatic and alicyclic backbones.

The inventive composition forms a continuous or discontinuous layer thereof associated with the substrate to be protected. Preferably, then, the inventive composition is "film-forming" in that it forms a film, which preferably is continuous, recognizing that discontinuous films may provide adequate protection against certain pest species under certain circumstances. The inventive coating composition also can contain adhesive ingredients (e.g., low Tg resins, tackifiers, etc.) that render it a conventional "adhesive" in order to adhere well to certain structures and to even join two structural surfaces together. Moreover, by careful formulation, the inventive composition may exhibit the thixotropy and adhesive characteristics to render it a caulk or sealant and, thus, protect cracks in structures. Thus, the term "composition" is to be construed broadly for present purposes in that the inventive pest species barrier composition may perform as a coating on the structure to be protected even if it conventionally also may termed an adhesive, caulk, sealant, or other designation.

With respect to the target organisms, the problem is that many organisms may be considered pets or benign under some circumstances, and pests under other circumstances. Frequently, a non-pest becomes a pest because it is in a location that humans define as inappropriate. The location may be acceptable, but the organism may be engaged in an activity that humans define as inappropriate. The damage done may be related to health, damage to property, esthetics, etc. Different cultures view certain organisms quite differently. Organisms fit into ecosystems, and exterminating a given species could have very undesirable overall results.

Thus, for present purposes, the invention defines "pest" in terms of:
1. species, and
2. location, and
3. activity to be controlled, and
4. damage to health/property/esthetics.

In the context of the present invention, the pest control agent emphasizes the location that prevents termites and other species from entering. A deer is a pest in this context, because a deer can facilitate a termite's breach of the barrier set up by the inventive system. A termite is not a pest if it is consuming dead wood in a forest. Roaches, termites, fire ants as well as clams, Zebra Mussels, and snails all play important and critical roles in the ecosystem; but in the wrong place relative to our homes and businesses (e.g., like generating energy in power plants or protecting our landscaping from the deer browsing on it), they are then condemned as a "pest". Thus, organisms are undesirable in the human definition based upon damage to structures, materials, or reduction in yield of a desirable crop species by the invasion of an undesirable pest species into the farmers' field.

For present purposes, then, the terminology "pest species" will be used to identify those (unwanted) organisms that are to be controlled. That is, "pest termites" are termites that attack buildings. "Pest deer" invade our urban space. When termites and deer occupy their natural habitats, they are not "pests" for present purposes.

Pest species, then, can include, inter alia, microbes, fungi, algae, bacteria, viruses, spores, insects, birds, animals (land and sea), rodents, and the like. Specific such pest species include, inter alia, termites, ants, boring wasps, deer, squirrels, mice, rats, mollusks (clams, oysters, mussels), and the like. For present purposes also, a "pesticide" is an active control agent or ingredient that repels, attracts, or kills pest species that are harmful to wood and wood-containing products. So long as the pest species does not invade the wood product, the control agent has accomplished its intended purpose, regardless of the mechanism of its action.

Advantages of the present invention include an inexpensive and convenient method for applying a pest control agent, which protects (e.g., wooden) structures. Another advantage is the protection of the wooden structures for relatively great lengths of time ranging from 1 to more than 30 years. A further advantage is that this protection is provided to the structures immediately upon the application of the pest control agent without allowing the release of the pest control agent to the environment in quantities that may have the potential to harm human beings or other desirable life forms which may come into contact with the wood destroying or wood decaying barrier. These and other advantages will be readily apparent to those skilled in the art based on the present disclosure.

BRIEF DESCRIPTION OF THE DRAWING

For a fuller understanding of the nature and advantages of the present invention, reference should be had to the following detailed description taken in connection with the accompanying drawings, in which.

DETAILED DESCRIPTION OF THE INVENTION

Figure 1:
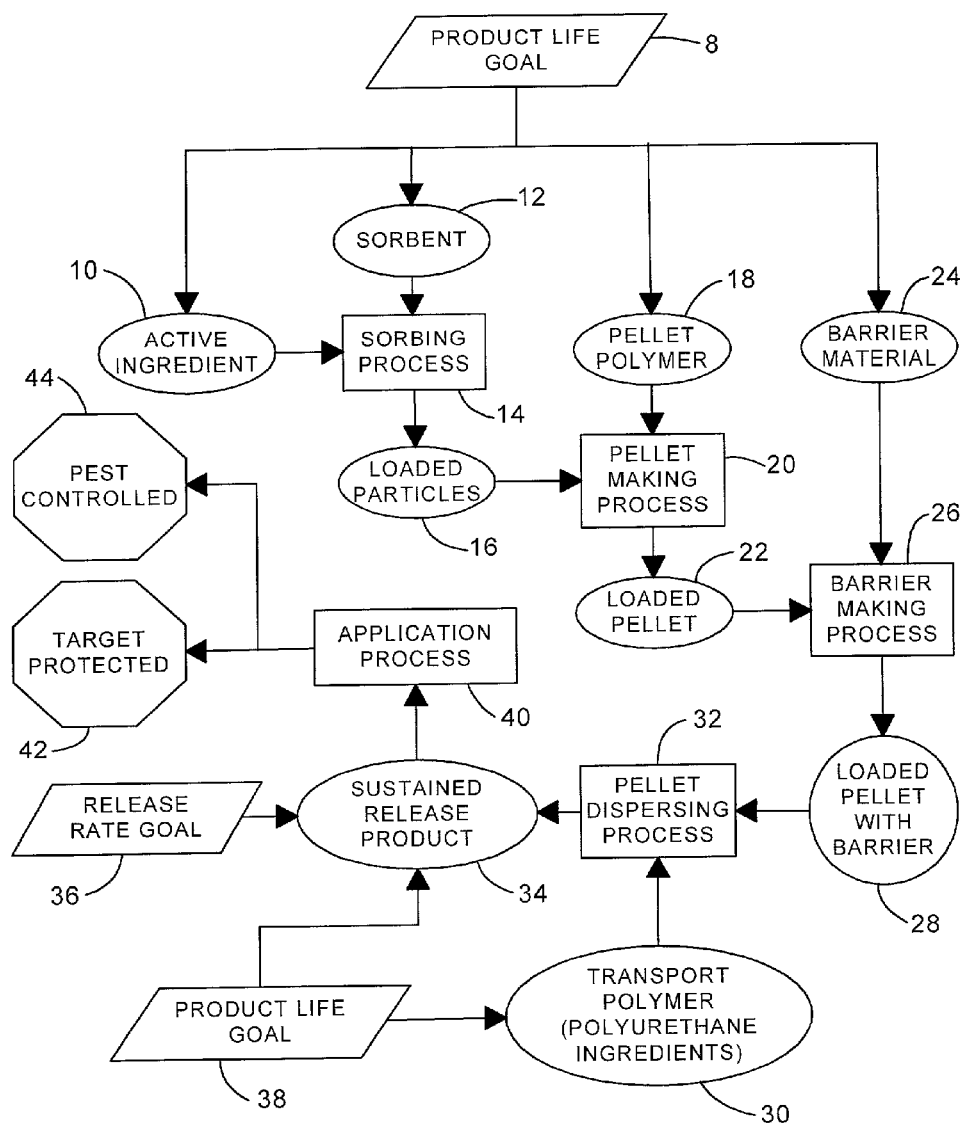
FIG. 1 is a schematic flow diagram for synthesizing the polymer pellets used in compounding the pest control barrier compositions of the present invention. It will be described in detail below.

The present invention displays numerous features in that an active ingredient is contained in a polymer pellet that optionally is coated with a barrier material that acts as membrane that allows the active ingredient to move to its surface. The pellet is contained in a polyurethane matrix that also acts as membrane that allows the active ingredient to move to its surface. The active ingredient on the surface controls (e.g., repels or poisons) selected (targeted) pest species that approach or touch the surface. The products of this invention provide sustained effective performance over many years. The products of this invention also can be applied by spraying, roller coating, or by other coating techniques. These products further can protect cracks, gaps, and other irregular surfaces, in addition to floors, walls, and other conventional surfaces. To protect structures further, the composition can be admixed with soil, vermiculite, or perlite, and distributed in the soil around the structure to disturb an oft used pathway of pests.

General Product Features

In order to achieve these features, the invention faces several challenges. The barrier coating of the pellet must retain its barrier properties over many years, but the active ingredient must dissolve in the barrier polymer in order to reach the polyurethane phase. If too much of the control agent dissolves or if it dissolves to rapidly, the barrier is compromised. Then, the product could fail. Polyurethanes face environmental challenges because they have sensitive functional groups that are attacked by water, oxygen, microbes, acids, alkalis, and sunlight. Degradation of the polyurethane matrix could cause product failure. These challenges are inventionally addressed and solved as will be described below.

Pellet Design

Referring initially to FIG. 1, the sustained release system disclosed herein is illustrated. Initially, the product life goal, 18, determines the ingredients used and system constructed. Based on product life goal, 18, the active ingredient of pesticide, 10, and a sorbent, 12, which is not soluble in the pellet polymer, are sent to an incorporating (e.g., sorbing) process, 14, whereat pesticide 10 is incorporated by sorbent 12. Desirably, sorbent 12 is in the form of small particles of nominal size ranging from about 100 microns to 12,700 microns (0.5 in) units in size. An inorganic sorbent (e.g., silica, carbon, an aerogel) or an organic sorbent (e.g., a polymer that strongly attracts the active ingredient) can be used to incorporate active ingredient 10. The loaded particles, 16 (pesticide 10 and sorbent, 12, are combined with a pellet polymer, 18, and sent to a pellet making process, 20, from which (active ingredient) loaded pellets, 22, are produced. Sorbent 12 releases active ingredient 10 into the pellet polymer (e.g., polyethylene, polypropylene, polyethylene terephthalate, or polyurethane elastomer). The volume of this layer, pellet polymer 18, is selected to provide a concentration of active ingredient 10 that is below the failure threshold for pellet polymer 18.

In some embodiments of this system, active ingredient 10 is incorporated into pellet polymer 18 during pellet-making step 20. No sorbent 12 would be needed. Examples of this short cut include, inter alia, epoxy resins, unsaturated polyester resins, and block copolymers of epoxy or silanol intermediates with polyurethanes terminated with isocyanate groups that would serve simultaneously as polymeric sorbents and pellet polymer.

At this point in the process, loaded pellets 22 optionally can be coated with a barrier material, e.g., polyvinylidene chloride (PVdC). In order to accomplish this, loaded pellets 22 and a barrier material, 24, are passing into a barrier making process, 26, for coating or encapsulating loaded pellets 22 with barrier material 24. This coating is applied, for example, in a liquid fluidized bed of pellet particles 22 or by other suitable means. The thickness of the coating ranges from relatively thin to quite thick, for example, from about 1 μm to 75 μm. This results in a product that provides sustained release of active ingredient over many years of product use. Alternative pellet barrier coatings include, for example, amorphous nylon, ethylene-vinyl alcohol, epoxy resins, and unsaturated polyesters.

The resulting loaded pellets with barrier, 28, along with transport polymer, 30, e.g., polyurethane ingredients, are send to a pellet dispersing process, 32, to produce a sustained release product, 34. During this process, a small amount of active ingredient may be released into the transport polymer, which is desirable in providing immediate usefulness. If this release does not occur, a small amount of active ingredient may be added at this stage. In designing sustained release product 34, criteria that must be met include, inter alia, a release rate goal, 36 and a product life goal, 38. Product life goal 38 also impacts the ingredients chosen to synthesize transport polymer 30. Sustained release product 34 then is sent to an application process, 40, which is determined by both the target to be protected, 42, and the pest species to be controlled, 44.

In some embodiments of this invention, transport polymer 30 may be made of a polyurethane that is so highly crystalline and/or crosslinked that transport polymer 30 itself also serves as a barrier in place of barrier material 24. An example of this type of material is described in U.S. Pat. No. 5,352,754 as a primarily hard segment polyurethane. In an advantageous embodiment of the present invention, active ingredient 10 is dispersed in a polymer (e.g., HDPE) and then molded into pellets without use of a barrier coating. This cheaper pellet is dispersed into this high performance polyurethane.

In some other embodiments of this invention, transport polyurethane 30 is tailored to be so highly crystalline and/or crosslinked that the active ingredient is dispersed in the polyurethane without use of pellets. In this case, the chemical structure of active ingredient 10 determines at which point in the process that this ingredient is added to the formulation. That is, reaction of active ingredient 10 with isocyanate groups or amines is avoided by waiting until the process is partly completed.

Durable Polyurethanes

The polyurethanes that are preferred for this invention are designed to overcome the environmental challenges by use of one or more of the following methods. Hydrolysis is a major challenge. The present invention reduces exposure to water required for hydrolysis by designing the surface of the product to be hydrophobic. Therefore, very little water will stay in contact with the surface. Aromatic isocyanates are replaced with aliphatic or alicyclic isocyanates, and polyols that contain ester or ether linkages are replaced with aliphatic or alicyclic diols. These changes make the product much more durable. Other approaches to fight hydrolysis include use of such drying agents as molecular sieves or silica to tie up water that does pass through the surface of the product.

The products of this invention will be used frequently to coat concrete, masonry, and like surfaces, which often can serve as pest species pathways to wood and wood products. Fresh concrete contains an excess of lime that makes it highly alkaline. The inventive pest species control product can be tailored to overcome this alkaline hydrolysis challenge by using the hydrophobic surface approach.

Microbes are major agents that cause hydrolytic or oxidative damage. Therefore, the inventive pest species control product may include antimicrobial active ingredients, as well as other pesticides.

Rodents, deer, and other large pest species may gnaw on the object that the inventive pest species control product is designed to protect. In such circumstances, one of the active ingredients will be an irritant, such as powdered pepper or pepper extract. Alternatively, bitter-tasting substances, such as those used in denaturing ethyl alcohol, could be used.

Exposure to sunlight can trigger several types of environmental degradation. Photochemical oxidation attacks polyurethanes that are based on aromatic isocyanates especially. Therefore, aromatics are replaced with aliphatic or alicyclic ingredients. Polyetherdiols have ether linkages that are subject of oxidative degradation. These vulnerable ingredients are replaced by aliphatic or alicyclic diols. Alternatively, pigments and/or UV absorbers also can be used to reduce the effects of sunlight.

Structures that are to be protected over time spans of decades develop cracks due to mechanical stresses. These cracks could affect the performance of the products of this invention. The polyurethanes of this invention also can be tailored to have adhesive properties to reduce the occurrence and adverse effects of cracking.

Embodiment #1: Compositions Rich in Polyureas

The sprayability and longevity needed for some applications of this invention cannot be attained with conventional polyurethane technology in which isocyanates are reacted only with polyols. The polymerization time is too long and the degree of crosslinking is not sufficiently high. In this invention, most or all of the polyol is replaced with amine-containing ingredients. In such cases the transport polymer will predominate in urea groups, rather than urethane groups. Alternatively, thiols could serve as the active hydrogen reactive groups in place of hydroxyl (polyol) groups.

Thus, one or more isocyanate ingredients such as toluene diisocyanate (TDI), methylene diphenyl diisocyanate (MDI), polymeric methylene diphenyl diisocyanate (PMDI), hexamethylene diisocyanate (HDI), or isophorone diisocyanate (IPDI) is reacted with a separate mixture comprising one or more amine-containing ingredients, such as, for example, 4,4'-methylene dianiline, 1,4-diaminocyclohexane, 2,4-diaminotoluene, 2,6-diaminotoluene, or 1,4-diaminohexane. The active ingredient that may be incorporated into a pellet is combined with this amine component. The amine formulation also can include some polyols, diols, and catalysts to adjust the physical properties (e.g., modulus) of the polymer, the rate of reaction, and to reduce unit costs. The reactants are kept separate in a two-component spraying system until time for reaction because the gel time may be as little as 5 seconds. The spraying method disclosed in U.S. Pat. No. 6,250,567 may be useful for this application.

The polymer made by this process contains mostly urea linkages, instead of mostly urethane linkages that are formed in conventional urethane polymers. Urea linkages are more resistant to hydrolytic reactions that are the major causes of polymer degradation. Therefore, the polymer of this invention is more likely to last longer than conventional ones.

Crosslinking of the type only possible with urea linkages further increases the longevity of this product. The ratio of isocyanate to amine is selected so that there is some excess isocyanate present. This excess then reacts with active hydrogen atoms in the initial polymer to yield biuret crosslinking. Biuret crosslinking is known to be more stable than the allophanate form of crosslinking (Szycher, M., *Szycher's Handbook of Polyurethanes*, pp. 4–9, CRC Press, Boca Raton, 1999).

Crosslinking also increases the molecular weight and reduces the free volume of the polymer structure. The resulting structure reduces the rate of release of the active ingredient and prolongs the life of the product by reducing the rate of permeation of moisture into the structure.

Although this process is especially useful for spray systems, it can be adapted for roller coating and other coating systems. For this purpose, use of more sterically hindered isocyanates (e.g., 2, 4'-MDI) would be desirable.

Embodiment #2: Compositions Rich in
Aliphatic/Alicyclic Moieties

Many applications of this invention do not expose the product to sunlight. However, protection of utility poles, wharves, fence posts, and some parts of buildings do expose the product to sunlight that contains significant UV radiation. Products that use MDI, TDI, and other aromatic isocyanates are likely to fail due to photo-oxidation and other free radical-initiated reactions. Aromatic isocyanates absorb UV radiation in the range of 220 nm to 300 nm. Various UV absorbing additives could be used to alleviate this problem, especially if long product life is not a goal. However, longevity is a major goal for the products of this invention. Accordingly, polymer design can be used to increase the UV resistance of the inventive pest species control system.

Isocyanate Component

Polyurethanes made from aliphatic and alicyclic isocyanates are known to resist yellowing upon exposure to sunlight because they do not absorb UV radiation, in contrast to those made with aromatic isocyanates. The preferred aliphatic isocyanates include, for example, 1,6-hexamethylene diisocyanate (HDI) and 1,4-tetramethylene diisocyanate. Preferred alicyclic diisocyanates include, for example, hydrogenated methylene diphenyl diisocyanate, 1,4-cyclohexane diisocyanate, and isophorone diisocyanate.

Longevity in all uses is enhanced by the increased hydrophobicity of the non-aromatic isocyanates. It is further enhanced if the non-aromatic isocyanates are used in a formulation that yields a product that has a low percentage of soft segments. Soft segments contribute to water absorption that reduces longevity. A soft segment in polyurethanes is defined as a portion of the polyurethane molecule that is amorphous or low in crystallinity. Such regions usually arise from the polyol component. They can be caused by use of long-chain polyol ingredients or by using shorter chains but having frequent amorphous regions. In this invention, the formulator uses short-chain polyol ingredients (e.g., polypropylene glycols with MW<1000, preferably about 300 daltons). The formulator also limits the polyol content to less than about 20%. In some embodiments, diamines are substituted for polyols.

Soft segments not only contribute to water absorption, but also to elongation and elasticity. The longevity benefits that are attained from low soft segment content have to be balanced with the need for some flexibility in the coating product, as is true with all coatings.

Effects of Crystallinity and Cross-Linking

The hard segments of the polymer chain are crystalline or crosslinked. They resist permeation by water and oxygen. This barrier attribute contributes to the longevity of the product. The barrier attribute applies also to the active ingredient so that the release rate is reduced by the presence of hard segments.

The sensitivity of the carbonyl groups in these polymers to UV radiation is reduced by the hydrogen bonding that is involved in crystalline domains of polyurethanes (Szycher, M., *Szycher's Handbook of Polyurethanes*, pp. 2–10 to 2–20, CRC Press, Boca Raton, 1999). Therefore, crystallinity enhances the longevity of the products of this invention.

The hard segments also contribute to the rigidity of the product. Because some flexibility is needed, an upper limit is set for the percentage of hard segments. There are six types of crosslinks, some of which can be broken under stress and re-formed. The six types of crosslinking are:

1. Use of isocyanates with functionality greater than 2 creates crosslinks between polymer chains. A commercially available example is polymeric methylene diphenyl diisocyanate (PMDI), which has an average number of isocyanate groups that is between 2 and 3. Another commercially available isocyanate with functionality greater than 2 is the product obtained by reaction of HDI with water. It has a functionality of 3.
2. Use of low molecular weight polyols with functionality greater than 2 creates tight crosslinks between polymer chains. These crosslinks are involved in generating hard segments in the polyurethane. Examples of hydroxy crosslinkers include trimethylolpropane, glycerin, and sorbitol.
3. Use of polyols with functionality greater than 2 also creates crosslinks between polymer chains. The tightness of polyol crosslinking is less than that achieved with isocyanates or low molecular weigh polyols because the polyol chains are much longer. Examples of polyols with a functionality of 3 include glycerin polyether triols, and trimethylol propane polyether triols. Hydrogenated castor oil, which has a functionality between 2 and 3, is a polyester that has crosslinking capabilities.
4. In a system in which the molar equivalents of the diol are reacting with the isocyanate, there is still an opportunity for crosslinking by allophanate formation. The hydrogen of the —NH group of a urethane can react with an isocyanate group associated with another chain which forms a branching at this point. This means that a hydroxyl group somewhere in the polymer does not have an isocyanate partner. Thus, the polymer becomes crosslinked, but it also has developed some weak points where hydroxyls are not reacted. However, the formulation can be modified to have an excess of isocyanate groups above that required by stoichiometry in order to accommodate such unreacted hydroxyl groups. Then, allophanate crosslinking can be used without leaving unsatisfied hydroxyls. Use of vaporous amine catalysts would be desirable to obtain the most complete reaction of the residual hydroxyls (for example, U.S. Pat. No. 4,517,222).
5. Reaction of isocyanate with water yields free amine groups, which are much more reactive with isocyanate groups, so that di-substituted urea groups are formed. These ureas also can react with isocyanate groups to form highly stable biuret groups. Thus, astute use of moisture can cross-link the polyurethane to make it more resistant in the environment. Instead of using the reaction of water with isocyanate to make the amine, it may be more desirable to manufacture the polyurea more directly as described above wherein isocyanate compounds are reacted with amine compounds, which then is added to the isocyanate cross-linkers to form polyureas. Then, the crosslinking amine need not be the one that results from reaction of the isocyanate with water.
6. Virtual Crosslinking via Hydrogen Bonding is associated with the development of hard segments. This concept allows a product to have a higher percentage of hard segments than would be possible in conventional polyurethane systems. Hydrogen bonding "virtual" crosslinks are reversible and, therefore, of value to this embodiment of the invention. The major hydrogen bonds are those between —NH and —C=O groups located in separate chains of the polymer.

Polyol Component

Almost all commercial polyurethanes make use of polyols that are hydroxy-terminated polyesters or polyethers. The presence of the ester and of ether linkages facilitates the penetration of water or oxygen into the polyurethane. One embodiment of this aliphatic/alicyclic embodiment is the replacement of some or all of the polyester/polyether moieties with aliphatic and/or alicyclic moieties. For example, butadiene can be polymerized to make a polybutadiene that can be converted to hydroxy-terminated aliphatic compounds. This butadiene-derived diol then is reacted with HMDI to generate polyurethanes that are very hydrophobic (Ma, et al., "Mechanical Properties of Hydrophobic Urethane Elastomers", *ACS Polymer Division Preprints,* 2000, page 380–381). These polyurethanes show considerable enhancement of barrier properties and have good modulus, even though they contain 60% to 85% of the soft segment ingredient.

The aliphatic or alicyclic polyol component of the polyurethane of this invention includes the diol described above and other diols as follows:
1. straight chain hydrocarbons that have 8 to 30 carbons with hydroxyl groups at each end;
2. carbocyclic rings that contain from 5 to 32 members with hydroxyl groups that are not on adjacent carbons; and
3. molecules that have one or more rings, as defined in item 2 immediately above, that have two straight chain hydrocarbon chains that are substituents, with two hydroxyl groups are present, one at the end of each pendent chain.

Thus in this invention, alicyclic/aliphatic isocyanates are employed in ways that generate polyurethanes with a high percentage of hard segments. Use of a limited percentage of short-chain polyols and added diamines or triamines promote crystallization and virtual crosslinks that are needed to have high percentages of hard segments without being overly rigid. The invention also includes the use of polyols that are not derived from polyesters or polyethers but which are aliphatic and/or alicyclic ingredients (U.S. Pat. No. 5,043,484). The added hydrophobicity can provide much longer product life.

Two additional sources of hydroxyls for reaction with isocyanate-terminated polyurethanes are silanol and epoxy intermediates. Thus, block copolymers can be made by reacting silanols with polyurethane prepolymers that have free isocyanate groups. Silanols have silicon atoms attached to hydroxyl groups. Epoxy resins cure to provide hydroxyl groups that are reactable with isocyanate groups. These block copolymers also have been made and found to be useful in medical devices (see Szycher, supra).

Embodiment #3: Pellets for Prolonged Sustained Release of Active Ingredient

This pest species control system includes the active ingredient(s) incorporated into a sorbent(s), the polymer phase, and the pellet shell (FIG. 1). The active ingredient moves through the pellet, into a matrix of transport polyurethane to the surface of the product where it provides its service. This embodiment focuses on the pellet subsystem. The active ingredient is a pest species control agent as defined above.

Sorbents (sorbent 12 from FIG. 1) are selected from the ingredients that include, inter alia, silica; carbon; aerogels; oxides of metals; and oxides, carbonates or phosphates of Group 2 metals. The sorbents are selected for their ability to incorporate and release large amounts of active ingredient 10. This implies a large surface area per unit volume. The sorbent also must not cause degradation of the active ingredient to a significant extent.

Suitable pellet polymers are selected based on their ability to attain sufficient concentration of the active ingredient to pass it through the barrier and to have a partition coefficient with the sorbent such that a desirable release rate can be attained. Suitable polymers include, for example, polyethylene, polypropylene, polybutenes, natural rubber, polyisoprene, polyesters (such as, for example, polyethylene terephthalate and polyethylene adipate), styrene butadiene rubber, polyacrylates, polymethacrylates, and polyurethanes.

The polyurethane composition that is best suited for the pellet is usually not the same as the one that is chosen for the polymer that transfers the active ingredient to the surface. For example, the pellet polymer could be a purchased thermoplastic elastomer. The polymer could be melted and blended with the particles of sorbent that contain the active ingredient. The polyurethane is not being synthesized simultaneously as the pellet is being manufactured; therefore, there are no free isocyanate groups that could react with the active ingredient.

The barrier material is selected to adjust the release rate to a level that meets the longevity goals, while also meeting the requirements for active ingredient concentration. In addition, the barrier polymer needs to retain these properties over the life of the product. Relatively few polymers meet this stringent set of requirements. The leading candidates are polyvinylidene chloride (PVdC), dry polyethylene polyvinyl alcohol copolymer (PVOH), amorphous Nylon 6, liquid crystal polymers, crosslinked elastomers, plasma-treated polyolefins, epoxy resins, and unsaturated polyesters. The barrier layer may be applied as a finished product or it may be a reactive coating. Typical reactive coatings include amine curable materials (epoxies) or free radical cured elastomers (e.g., unsaturated polyesters). Further information on barrier materials can be found in "Barrier Polymers and Structures", edited by W. J. Koros, *ACS Monograph* 423, American Chemical Society, Washington, D.C. (1990).

The pellet content of the system must contain enough active ingredient to release at a rate that is adequate to repel the target pest species for a period of time that meets the longevity goals. For example, if the release rate is one nanogram/daycm$^2$ for 30 years (ca. 11,000 days), then the pellets must store at least 0.11 mg for each square centimeter of surface area. The concentration of active ingredient in the pellet polymer additionally must not exceed a threshold level that would cause barrier failure.

These elements of the system can operate in several modes that depend on the specific application. The following modes summarize the processes of this invention as described above.

1. As shown in FIG. 1, active ingredient 10 is incorporated onto (into) selected sorbent 12. Sorbent 12 in turn releases active ingredient 10 into a buffer layer of pellet polymer 18. The volume of this layer is selected to provide a concentration of active ingredient 10 that is below the failure threshold for the barrier coating.
2. The barrier coating that is applied to the pellet that contains the active ingredient is chosen to be a dispersion of polyvinylidene chloride (PVdC). This coating is applied in a liquid fluidized bed of pellet particles or other suitable means. The thickness of the coating ranges from relatively thin to quite thick (e.g., 1 μm to 75 μm). This results in a product that provides sustained release of active ingredient over many years of product use.

3. Alternative pellet types include epoxy resins and unsaturated polyesters. The active ingredient is incorporated into the pellet during its formation. No barrier coating would be needed.
4. In some embodiments of this invention, the polyurethane is tailored to be so highly crystalline and/or crosslinked that the pellet needs to have little barrier properties. An example of this material is described in U.S. Pat. No. 5,352,754 as a primarily hard segment polyurethane. In the present invention, the active ingredient is dispersed in a polymer (e.g., HDPE) and then molded into pellets without use of a barrier coating. This cheaper pellet is used with this high performance polyurethane.
5. In some other embodiments of this invention, the polyurethane is tailored to be so highly crystalline and/or crosslinked that no pellet is needed. That is, the hard and soft domains of the polyurethane are tailored to permit one polymer to perform the functions that usually require separate polymers. Therefore, the active ingredient is dispersed in the polyurethane without use of pellets. In this case, the chemical structure of the active ingredient determines when this ingredient is added to the formulation. That is, reaction of the active ingredient with isocyanate groups or amines is avoided by waiting until the process is partly completed.

Pest Species Control Agents

Acceptable insecticides include those insecticides approved by the U.S. Environmental Protection Agency to kill or repel termites, ants, other boring insects, and wood decaying microorganisms. The class of insecticide which is presently preferred for use in the present invention are pyrethrins, including tefluthrin, lambdacyhalothrin, cyfluthrin, deltamethrin, cypermethrin, permethrin, and natural permethrin. It will, however, be recognized by those skilled in the art that other effective insecticides such as isofenphos, fenvalerate, cypermethrin, permethrin, natural pyrethrin, organophosphate type insecticides, repellents as well as naturally occurring chemicals that act as irritants such as skunk oils and extracts of pepper can also be used. These insecticides are available from a number of commercial sources such as, for example, Dow Chemical Company, Mobay, ICI, Velsicol, Novartus, Syngenta, and FMC, respectively.

Insecticides, pesticides, pest species repellents, alone or in combination with one and another, or in combination with other bioactive ingredients, such as fungicides, may also be used in accordance with the present invention. Combinations of insecticides, pesticides, repellents, nematicides (also referred to as nematocides), and fungicides additionally may be used to advantage. Fungicides include, for example, carboximide, dicarboximide, diflumetorim, ferimzone, chloropicrin, pentrachlorophenol, tri-chloronitromethane, 1-3 dichloropropane, and sodium N-methyl dithiocarbomate. Nematicides include 1,3 dichloropropene, ethoprophos, fenamiphos, benfuracarb, and cadusafos.

Commercial molluscicides include, inter alia: Niclosamide (Bayluscide) from Bayer; Clamtrol from Betz; Calgon H-130 from Calgon, and Mexel 432 from RTK Technologies. These products are intended for controlling Zebra Mussels that cause water intake problems for electric power plants and/or the snails that carry Schistosomiasis. Copper compounds, e.g., cuprous oxide, has been a favorite leachable component of antifouling paints. Insoluble cuprous chelates could be active ingredients that bloom to the surface and stay there repelling fouling organisms. Commercial antifouling paints (e.g., SIL MAR) that feature silicone ingredients make the surface too slippery for fouling organisms to form a stable biofilm. Organotin compounds are known to work, but present toxicity issues. Copper compounds are seen to present toxicity issues too. Organic antifouling agents, such as are disclosed in U.S. Pat. No. 5,441,743, may be used to advantage too. Endod, a natural plant extract from the soap berry bush, contains the saponin, lemmatoxin. Endod has been used to control Zebra and Quagga Mussel infestations.

Application of the Pest Species Control Agent

Catalysts also may be added to some of the polyurethane systems to lower the reaction temperature down to levels more easily tolerated by the pesticide. For example, a suitable catalyst may drop the reaction temperature of polymerization from about 160° C. to about 120° C. Suitable catalysts include homogeneous and heterogeneous catalysts. Heterogeneous catalysts are usually provided as fine powders. Examples of suitable catalysts include, for example, tertiary amines, organometallic tin compounds, triethylene diamine, dibutyl tin dilaurate, dibutylbis(laurylthio)stannate, dibutyltinbis(isooctylmercapto acetate), dibutyltinbis(isooctyl maleate), dimethylcyclohexylamine, and 1,8-diazabiscyclo[5,4,0]undec-7-ene (DBU). Often, these catalysts are not added to the transport polyurethane ingredients until just before application.

To combine the sustained release product with the low temperature catalytic curing agent in a single application (e.g., spray application), the two are mixed together immediately prior to spraying, to prevent the clogging of the spray equipment. Preferably, the curing agent is combined with the sustained release product within the nozzle of a pressurized spraying device. However, applications wherein the sustained release product is combined with a low temperature catalytic curing agent prior to the introduction of the mixture into the spraying device are within the scope of the invention.

A great variety of suitable spraying devices are suitable for the practice of the present invention. For example, pages 158–170 of Oertel's, *Polyurethane Handbook,* published by Hanser in 1993 describe a variety of suitable mixheads. These devices are well understood by those having skill in the art, and no further elaboration of their operation is necessary to enable their use in the practice of the present invention. As contemplated by the present invention, any spraying device which will allow a liquid to be combined with pressurized gas (typically air) and expelled as a fine mist or droplet is acceptable, as are spraying devices which allow the delivery of liquid under pressure without air.

The pellets preferably are small enough to fit through the spray head of standard spraying equipment utilized in the spray application of the present invention, or below about, for example, $1/16^{th}$ inch in diameter and comprise the same pesticide bound within transport polymer matrix. These pellets may be produced in a manner similar to that described in U.S. Pat. No. 5,856,271.

It will be appreciated, however, that the versatility of the invention permits application by other techniques including, for example, roller coating, brush coating, dipping, spray curtains, and like conventional application techniques.

The coatings thus formed by the practice of the present invention will immediately begin releasing pesticide in sufficient quantities to deter the invasion of pest species through the barrier formed by these coatings. These coatings will also continue to release pesticide in sufficient quantities to deter the invasion of pest species for many years, in some cases for periods of thirty years or greater.

To enhance the safety of these coatings, a protective layer of ethylene vinyl acetate (EVA), polyvinyl alcohol (PVA), or a like material may also be applied thereover. The EVA also may be applied as a sprayed coating utilizing spray equipment well known by those having skill in the art. The EVA is applied in a second spraying on top of the polyurethane coating. The EVA coating provides a protective barrier to prevent humans and other non-target animals from coming into contact with the pesticide being released from the coating. The EVA coating also assists in enhancing the durability of the coating through its resistance to the effects of UV radiation.

In addition to EVA and PVA coatings, polyvinyl acetate latex coatings can be applied to the cured urethane product, using spray technologies employed to paint the interior of buildings. Copolymers of vinyl acetate with acrylic esters also are used to make latices that are promising for spray application. Styrene butadiene latex paints also can be spray-applied to protect humans from contact with the pesticide.

While the invention has been described with reference to certain preferred embodiments, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application all units are in the metric system and all amounts and percentages are by weight, unless otherwise expressly indicated. Also, all citations referred herein are expressly incorporated herein by reference.

The invention claimed is:

1. A sustained release coating composition for applying a barrier to a structure to prevent the infiltration of pest species, comprising:
   (a) a transport polyurethane polymer enriched in hydrophobic elements comprising one or more of non-aromatic isocyanate segments, being enriched by predominating in urea linkages, or containing hard segments and formed from a diisocyanate and a diol chain extender of up to 12 carbon atoms that has a molecular weight of less than about 1,000, wherein said diisocyanate is one or more of toluene diisocyanate (TDI), methylene diphenyl diisocyanate (MDI), polymeric methylene diphenyl diisocyanate (PMDI), hexamethylene diisocyanate (HDI), isophorone diisocyanate (IPDI) and said diamine is one or more of 4,4'-methylene dianiline, 1,4-diaminocyclohexane, 2,4-diaminotoluene, 2,6-diaminotoluene, or 1,6-diaminohexane; and
   (b) a pellet comprising a pesticide incorporated into a pellet polymer and dispersed in said transport polyurethane polymer, said pellet polymer being one or more of polyethylene, polypropylene, polybutenes, natural rubber, polyisoprene, polyesters, styrene butadiene rubber, polyacrylates, polymethacrylates, polyethylene terephthalate, epoxy resins, unsaturated polyester resins, or polyurethane elastomer wherein the pesticide is one or more of pyrethrin, tefluthrin, lambdacyhalothrin, cyfluthrin, deltamethrin, isofenphos, fenvalerate, cypermethrin, or permethrin.

2. The coating composition of claim 1, wherein said pesticide is incorporated by an inorganic sorbent and then dispersed in said pellet polymer.

3. The coating composition of claim 2, wherein said inorganic sorbent is one or more of silica; carbon; aerogels; oxides of metals; and oxides, carbonates or phosphates of Group 2 metals.

4. The coating composition of claim 1, wherein said pellets are coated with a barrier material.

5. The coating composition of claim 4, wherein said barrier material is one or more of polyvinylidene chloride, amorphous nylon, ethylene-vinyl alcohol, epoxy resins, and unsaturated polyesters.

6. The coating composition of claim 1, wherein said pellets range in particle size from about 100 microns to 12,700 microns.

7. The coating composition of claim 1, wherein said coating composition also contains one or more of powdered pepper, a pepper extract, an antimicrobial agent, pigments, ultraviolet radiation absorbers, molecular sieves, or silica gel.

8. The coating composition of claim 1, wherein an excess of polyisocyanate is used to form said reaction product, wherein said reaction product can be formed by moisture cure.

9. The coating composition of claim 1, wherein polyurethane polymer is formed from an aliphatic or alicyclic isocyanate.

10. The coating composition of claim 9, wherein said aliphatic or alicyclic isocyanate is one or more of 1,6-hexamethylene diisocyanate (HDI), 1,4-tetramethylene diisocyanate, hydrogenated methylene diphenyl diisocyanate ($H_{12}MDI$), 1,4-cyclohexane diisocyanate, or isophorone diisocyanate.

11. The coating composition of claim 9, wherein said polyurethane polymer contains hard segments made by one or more of;
   the use of polyisocyanates having greater than 2 isocyanate groups per molecule;
   use of polyol having a molecular weight of less than about 1,000 and greater than 2 hydroxyl groups per molecule;
   an excess of isocyanate is used;
   or reaction of said isocyanate with an amine.

12. The coating composition of claim 11, wherein said isocyanate is polymeric methylene diphenyl diisocyanate, and said polyol is one or more of trimethylolpropane, glycerin, Sorbitol, glycerin, polyether triols, trimethylol propane polyether triols, or hydrogenated castor oil.

13. The coating composition of claim 1, wherein polyurethane polymer is formed from an aliphatic or alicyclic polyol.

14. The coating composition of claim 13, wherein said aliphatic or alicyclic polyol is one or more of hydroxy terminated polybutadiene, straight chain hydrocarbons that have 8 to 30 carbons with hydroxyl groups at each end, carbocyclic rings that contain from 5 to 32 members with hydroxyl groups that are not on adjacent carbons, or carbocyclic rings that contain from 5 to 32 members that have one or more rings and that have two straight chain hydrocarbon chains that are substituents with two hydroxyl groups present, one at the end of each pendent chain.

15. The coating composition of claim 9, wherein polyurethane polymer is formed from an aliphatic or alicyclic polyol.

16. The coating composition of claim 1, which is applicable to said structure by one or more of spraying, roller coating, or brush coating.

17. The coating composition of claim 1, wherein said transport polyurethane polymer is one or more of a coating composition, a sealant, a caulk, or an adhesive.

18. The coating composition of claim 1, wherein said transport polyurethane polymer is synthesized from isocyanates with functionality greater than 2.

19. The coating composition of claim 1, wherein said transport polyurethane polymer is synthesized from low molecular weight polyols with functionality greater than 2.

20. The coating composition of claim 19, wherein said transport polyurethane polymer is synthesized from polyols, which are one or more of trimethylolpropane, glycerin, sorbitol, glycerin polyether triols, and trimethylol propane polyether triols.

21. The coating composition of claim 9, wherein polyurethane polymer is formed from an epoxy or silanol polyol that produces block copolymers.

* * * * *